United States Patent
Driemel et al.

(10) Patent No.: US 9,250,302 B2
(45) Date of Patent: Feb. 2, 2016

(54) ADAPTER FOR A DIRECT-CONNECTION HEAD COIL WITH ADJUSTABLE TILT ANGLE

(75) Inventors: Daniel Driemel, Oederan (DE); Hubertus Fischer, Bamberg (DE)

(73) Assignee: Siemens Aktiengesellschaft, München (DE)

( * ) Notice: Subject to any disclaimer, the term of this patent is extended or adjusted under 35 U.S.C. 154(b) by 750 days.

(21) Appl. No.: 13/554,878

(22) Filed: Jul. 20, 2012

(65) Prior Publication Data

US 2013/0023756 A1   Jan. 24, 2013

(30) Foreign Application Priority Data

Jul. 21, 2011   (DE) .......................... 10 2011 079 575

(51) Int. Cl.
  *G01R 33/28* (2006.01)
  *G01R 33/34* (2006.01)
  *A61B 5/055* (2006.01)
  *A61B 6/04* (2006.01)

(52) U.S. Cl.
  CPC .............. *G01R 33/28* (2013.01); *A61B 5/0555* (2013.01); *G01R 33/34046* (2013.01); *A61B 6/0407* (2013.01)

(58) Field of Classification Search
  CPC ............. G01R 33/28; G01R 33/34046; A61B 5/0555; A61B 6/0407
  See application file for complete search history.

(56) References Cited

U.S. PATENT DOCUMENTS

| | | | |
|---|---|---|---|
| 5,185,577 A * | 2/1993 | Minemura ..................... | 324/318 |
| 5,197,474 A * | 3/1993 | Englund et al. ............... | 600/415 |
| 6,037,773 A | 3/2000 | Mitsumata et al. | |
| 6,529,004 B1 * | 3/2003 | Young ........................... | 324/318 |
| 6,577,888 B1 * | 6/2003 | Chan et al. .................... | 600/422 |
| 6,784,665 B1 * | 8/2004 | Chan et al. .................... | 324/318 |
| 7,446,531 B2 * | 11/2008 | Schnell et al. ................ | 324/318 |
| 7,613,494 B2 * | 11/2009 | Hadley et al. ................. | 600/407 |
| 7,696,752 B2 * | 4/2010 | Takamori ...................... | 324/307 |
| 7,701,209 B1 * | 4/2010 | Green ........................... | 324/307 |
| 8,046,046 B2 * | 10/2011 | Chan et al. .................... | 600/422 |
| 8,055,326 B1 * | 11/2011 | Dworkin et al. .............. | 600/422 |
| 8,188,740 B2 * | 5/2012 | Ninomiya et al. ............. | 324/318 |
| 8,294,460 B2 * | 10/2012 | Driemel ........................ | 324/307 |
| 8,369,929 B2 * | 2/2013 | Scarth et al. .................. | 600/415 |
| 8,548,569 B2 * | 10/2013 | Piferi et al. ................... | 600/429 |
| 2005/0127914 A1 | 6/2005 | Eberler et al. | |

(Continued)

FOREIGN PATENT DOCUMENTS

DE   103 14 215 B4   11/2006
DE   10 2008 063 629 A1   7/2010

OTHER PUBLICATIONS

German Office Action dated May 4, 2012 for corresponding German Patent Application No. DE 10 2011 079 575.8 with English translation.

*Primary Examiner* — Dixomara Vargas
(74) *Attorney, Agent, or Firm* — Lempia Summerfield Katz LLC (57) ABSTRACT

An adapter for a local coil for a magnetic resonance tomography device is provided. The adapter is placeable on a patient support for the magnetic resonance tomography device. The adapter includes an adapter upper part that is removably connectable to the local coil. The adapter also includes an adapter lower part that is removably connectable to the patient support. The adapter also includes a tilt device, by which the adapter upper part is movable relative to the adapter lower part.

24 Claims, 6 Drawing Sheets

(56) References Cited

U.S. PATENT DOCUMENTS

| | | |
|---|---|---|
| 2007/0270683 A1 | 11/2007 | Meloy |
| 2009/0216110 A1 | 8/2009 | Piron et al. |
| 2010/0156420 A1 | 6/2010 | Driemel |
| 2013/0131498 A1* | 5/2013 | Taracila ........... G01R 33/34084 600/422 |
| 2013/0184563 A1* | 7/2013 | Driemel ............... A61B 5/0555 600/415 |
| 2015/0057527 A1* | 2/2015 | Driemel ........... G01R 33/34007 600/415 |
| 2015/0057528 A1* | 2/2015 | Driemel ............... A61B 5/0555 600/415 |
| 2015/0065852 A1* | 3/2015 | Driemel ........... G01R 33/34084 600/410 |

* cited by examiner

FIG 6 ic resonance device MRT
ADAPTER FOR A DIRECT-CONNECTION HEAD COIL WITH ADJUSTABLE TILT ANGLE This application claims the benefit of DE 10 2011 079 575.8, filed on Jul. 21, 2011.

BACKGROUND

The present embodiments relate to a head coil for a magnetic resonance tomography (MRT) system.

Magnetic resonance tomography devices for examining objects or patients using magnetic resonance tomography (MRT, MRI) are known, for example, from DE 10314215 B4.

In magnetic resonance tomography, images are conventionally recorded with a high signal-to-noise ratio (SNR) using coils (e.g., "local coils"). The coils are antenna systems that are mounted in immediate proximity on (anteriorly) or under (posteriorly) the patient. During an MRT measurement, the excited nuclei induce a voltage in the individual antennae of the local coil. The induced voltage is amplified with a low-noise preamplifier (e.g., LNA, preamp) and passed on via cables to the receiving electronics. In order to improve the signal-to-noise ratio, including with high resolution images, high-field systems are used (e.g., having field strengths of 1.5 T to 12 T and more). Since more individual antennae may be connected to an MR receiving system than receivers are present, a switching matrix (e.g., RCCS) is connected between the receiving antennae and the receiver. The switching matrix routes the currently active receiving channels (e.g., the channels that are currently in the field of view (FOV) of the magnet) to the receivers present. By this, more coil elements than receivers are present may be connected, since for whole-body coverage, only the coils that are in the FOV or the homogeneity volume of the magnet are to be read out.

The "coil" (or "local coil") may be an antenna system that may include one or more antenna elements (e.g., coil elements, an array coil). The individual antenna elements may be configured as loop antennae (loops), or butterfly or saddle coils. A coil includes coil elements, a preamplifier, further electronics (e.g., sheath current filters) and cabling, the housing and may include a cable with a plug, by which the coil is connected to the MRT system. The receiver (RX) provided on the system side filters and digitizes the signal received by the local coil and passes the data on to the digital signal processing unit. The digital signal processing unit may derive an image or a spectrum from the measurement and make the image or spectrum available to the user for diagnosis.

In order to position patients with abnormal changes to the cervical spine, for example, ankylosing spondylitis, wryneck, round back, or trauma patients, in head coils, the head coils may be raised (e.g., tilted) in a posterior region of the head, since the patient is not able to place the head flat in the coil in this position. For contacting systems that provide a defined relationship between the patient support and the head coil, for example, with "direct" contacting (e.g., contacting by plugging in plugs for power supply and/or for data lines) of the head coil to the patient support or with alternative contacting variants such as capacitive coupling between the patient support and the head coil, movement of the coil relative to the patient support is not possible in the plugged-in condition (e.g., if contacts of the local coil are plugged into contacts of the patient support). The coil and the patient support form a fixed plugged-together unit.

For coils that directly contact the patient support or for alternative contacting possibilities having a fixed relationship between the patient support and the coil, in the case, for example, of ankylosing spondylitis patients, a possible solution is changing the position of the patient with suitable mounting materials (e.g., a higher support for the pelvis). A further alternative solution is the placement of wedge-shaped parts under the head coil.

SUMMARY AND DESCRIPTION

The present embodiments may obviate one or more drawbacks or limitations in the related art. For example, a local coil for a magnetic resonance tomography system is further optimized. This is achieved efficiently and ergonomically.

An adapter is suitable, for example, for a local coil in the form of an MRT head coil. A configuration of the adapter according to the present embodiments enables a head coil that has contact directly into a patient support to be moved relative to the patient support in order to be able to examine patients with ankylosing spondylitis, wryneck or trauma patients or to be able to examine the patient in a position that is comfortable for the patient.

The adapter may have through contacting of electrical contacts to the patient support and to the head coil.

An embodiment of the adapter has, on an underside thereof, a replica of a direct plugging arrangement and of guide elements of the head coil. The adapter also has, on an upper side thereof, a replica of the direct plugging arrangement and of a guide on the patient support side in order to accommodate the head coil, so that the function may be adapted without changing existing hardware or local coils.

A divided adapter housing of the adapter including a patient support-side lower adapter housing lower part (e.g., adapter lower part) and an upper head coil-side adapter housing upper part (e.g., adapter upper part) enables by, for example, tilting an angular adjustment of the position of the head coil.

Flexible conductor connections between contacts of the upper and lower parts of the adapter support the mobility of the adapter upper part relative to the adapter lower part.

The movement and/or drive of the adapter upper part relative to the adapter lower part is carried out, according to one embodiment, by a screw mechanism that is able to fix an angle of the adapter upper part, once set, relative to the adapter lower part by the self-locking thereof.

A snap connection between the adapter and a head coil may enable common handling/movement of both parts, which is advantageous for the workflow/working with the adapter.

DETAILED DESCRIPTION OF THE DRAWINGS

Figure 6:
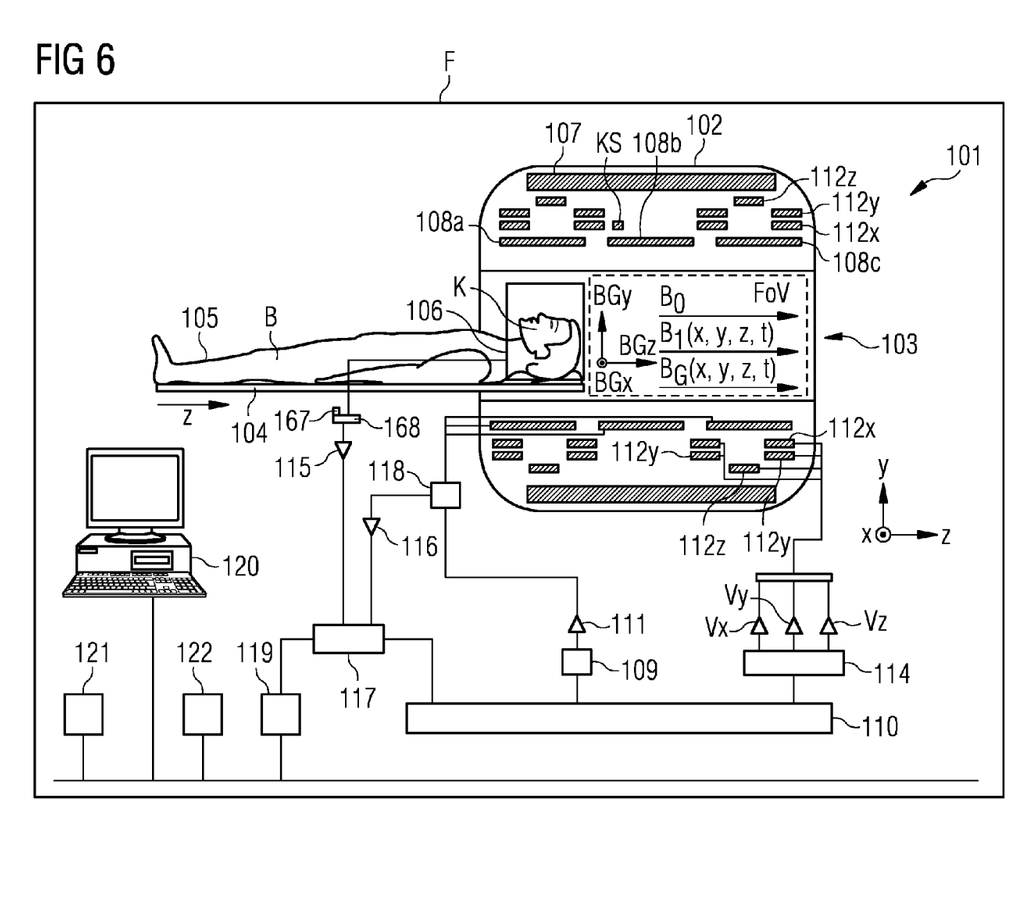
FIG. 6 is a schematic simplified representation of one embodiment of an MRT system.

FIG. 6 shows an imaging magnetic resonance device MRT 101 (e.g., arranged in a shielded room or Faraday cage F)

having a whole-body coil 102 with a chamber 103 (e.g., tubular chamber), into which a patient support 104 may be moved with a body of, for example, an object being examined 105 (e.g., a patient; with or without a local coil arrangement 106) in the direction of the arrow z in order to generate images of the patient 105 by an imaging procedure. Arranged on the patient (e.g., fastened with a belt) is a local coil arrangement 106 (e.g., fastened with the same or a further belt), with which in a local area (e.g., a field of view (FOV)) of the MRT, images of a partial region of the body 105 in the FOV may be generated. Signals from the local coil arrangement 106 may be evaluated (e.g., converted into images, stored or displayed) by an evaluation device (e.g., including elements 168, 115, 117, 119, 120, 121) of the MRT 101 connectable to the local coil arrangement 106 (e.g., via coaxial cable or by radio (element 167)).

In order to examine a body 105 (e.g., an object being examined or a patient) by magnetic resonance imaging with the magnetic resonance device MRT 101, different magnetic fields, the temporal and spatial characteristics of which are matched as closely as possible, are radiated onto the body 105. A powerful magnet (e.g., a cryomagnet 107) in a measuring cabinet having, for example, a tunnel-shaped opening 103, generates a static strong main magnetic field $B_0$ that has a strength, for example, in the range of 0.2 Tesla to 3 Tesla or more. A body 105 to be examined is moved, mounted on a patient support 104, into a region of the main magnetic field $B0$ that is approximately homogeneous in the FOV. Nuclear spins of atomic nuclei of the body 105 are excited via magnetic high-frequency excitation pulses $B1(x, y, z, t)$ that are radiated via a high frequency antenna shown highly simplified in FIG. 6 as a body coil 108 (e.g., a multiple part body coil 108a, 108b, 108c and/or a local coil arrangement). High frequency excitation pulses are generated, for example, by a pulse generation unit 109 that is controlled by a pulse sequence control unit 110. Following amplification by a high frequency amplifier 111, the pulses are fed to the high frequency antenna 108. The high frequency system shown in FIG. 6 is indicated schematically. In other embodiments, more than one pulse generation unit 109, more than one high frequency amplifier 111 and a plurality of high frequency antennae 108a, b, c are used in a magnetic resonance device 101.

The magnetic resonance device 101 includes gradient coils 112x, 112y, 112z, with which magnetic gradient fields are radiated during a measurement for selective slice excitation and for local encoding of the measurement signal. The gradient coils 112x, 112y, 112z are controlled by a gradient coil control unit 114 that, like the pulse generation unit 109, is connected to the pulse sequence control unit 110.

Signals emitted by the excited nuclear spins (e.g., of the atomic nuclei in the object being examined) are received by the body coil 108 and/or at least one local coil arrangement 106, amplified by associated high frequency amplifiers 116 and further processed and digitized by a receiving unit 117. The measurement data recorded are digitized and stored in a k-space matrix as complex numerical values. From the k-space matrix occupied by values, an associated MR-image may be reconstructed by a multi-dimensional Fourier transform.

For a coil that may be operated both in the transmitting mode and the receiving mode such as, for example, the body coil 108 or a local coil 106, the correct signal forwarding is regulated by an upstream transmission-receiving switch 118.

An image processing unit 119 generates, from the measurement data, an image that is displayed to a user via an operating console 120 and/or is stored in a storage unit 121. A central processing unit 122 controls the individual system components.

In MR tomography, images are recorded with a high signal-to-noise ratio (SNR) using local coil arrangements (e.g., "coils" or "local coils"). The coils are antenna systems that are arranged in the immediate vicinity on top (anterior), under (posterior), on, or in the body 105. During an MR measurement, the excited nuclei induce a voltage in the individual antennae of the local coil. The induced voltage is amplified with a low-noise preamplifier (e.g., LNA, preamp) and is forwarded to the receiving electronics. In order to improve the signal-to-noise ratio, including with high resolution images, "high field" systems (e.g., 1.5 T or more) are used. If more individual antennae may be connected to an MR receiving system than receivers are present, for example, a switching matrix (e.g., RCCS) is installed between the receiving antennae and the receivers. The switching matrix routes the momentarily active receiving channels (e.g., the channels that currently lie within the FOV of the magnet) to the receivers present. This allows more coil elements to be connected than there are receivers present, since with whole-body coverage, only the coils that are situated in the FOV or in the homogeneity volume of the magnet are to be read out.

A local coil arrangement 106 may be an antenna system that may include, for example, one or, as an array coil, a plurality of antenna elements (e.g., coil elements). The individual antenna elements are configured, for example, as loop antennae (e.g., loops), butterfly coils, flex coils, or saddle coils. A local coil arrangement includes, for example, coil elements, a pre-amplifier, further electronics (e.g., sheath current filters), a housing, supports and may include at least one cable with a plug, by which the arrangement is connected to the MRT system. A receiver 168 mounted on the system side filters and digitizes a signal received by a local coil 106, for example, via radio and transfers the data to a digital signal processing unit that may derive an image or a spectrum from the data obtained by a measurement. The digital signal processing unit makes the image or the spectrum available to the user, for example, for subsequent diagnosis by the user and/or for storage.

Some exemplary embodiments of MRT head local coils 106 are described below in greater detail making reference to FIGS. 1-5:

A patient 105 will undergo examination lying on a patient support 104 in an MRT 101 using a magnetic resonance tomography device head coil as the local coil 106 on the head K of the patient. A head height is adjustable (e.g., using the patient support), and/or the head inclination is adjustable (e.g., relative to the patient support) via an adapter 2.

Figure 1:
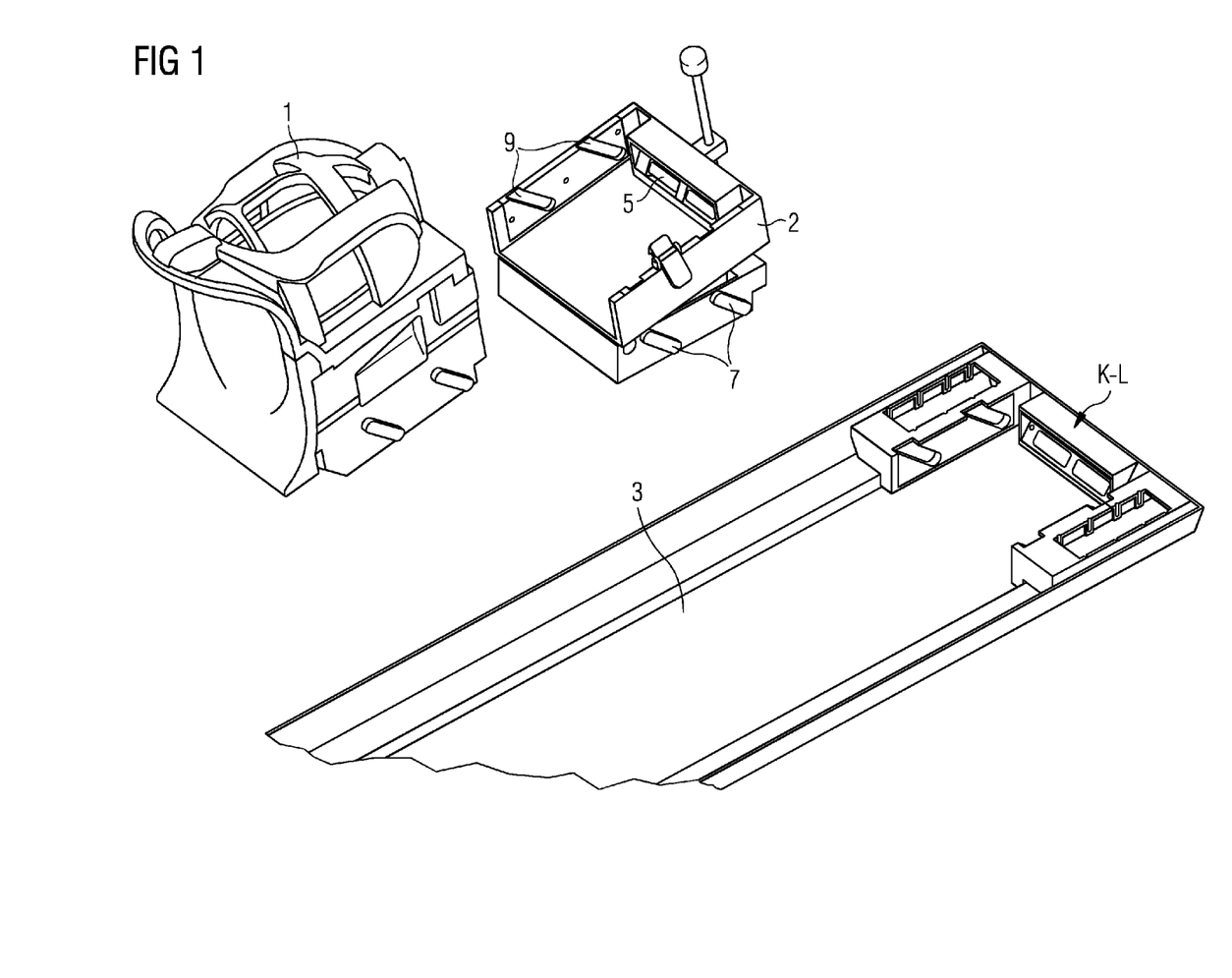
FIG. 1 is a perspective view of one embodiment of a head coil, an adapter, and a section of a magnetic resonance tomography (MRT) patient support.
Figure 2:
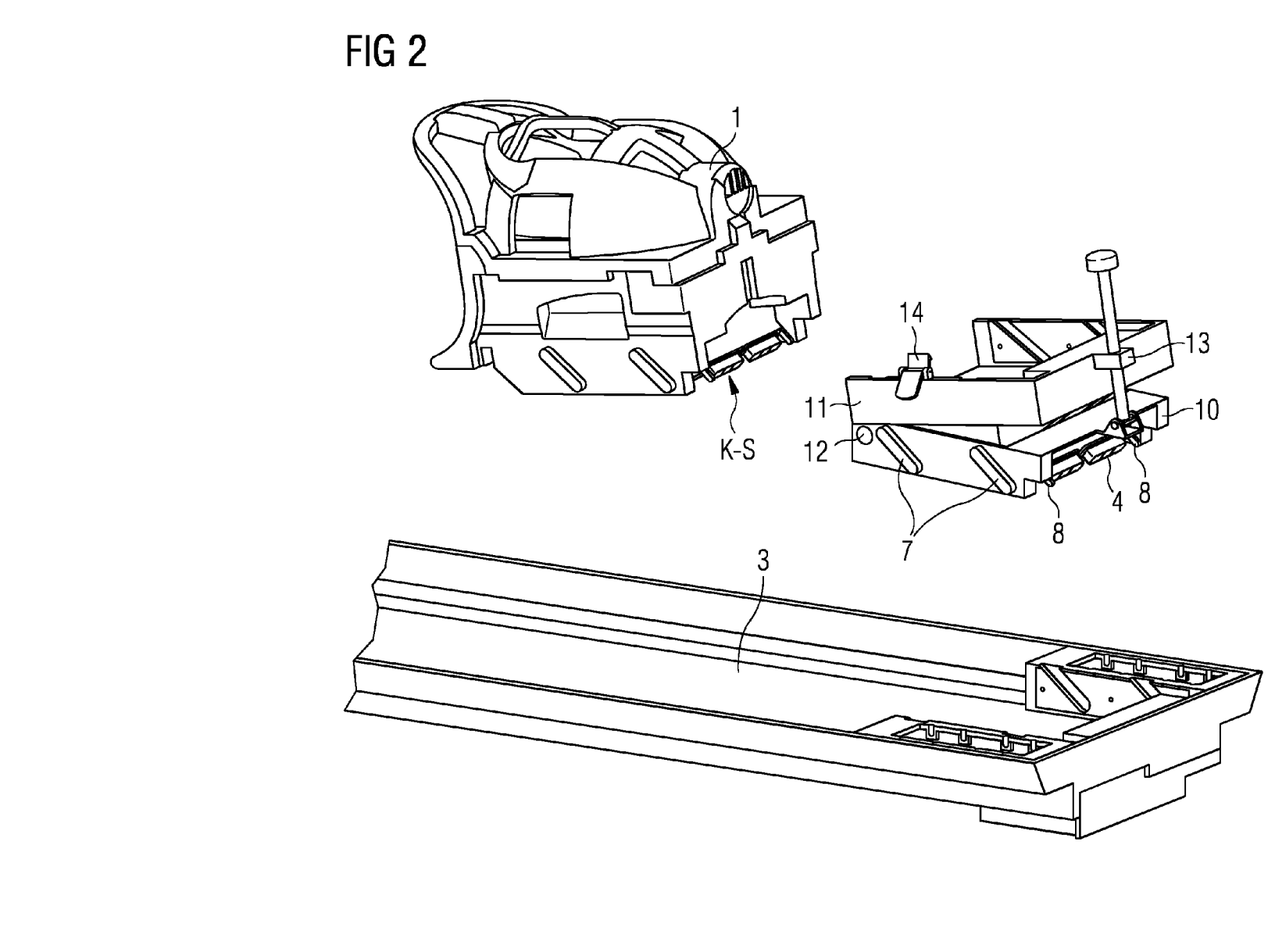
FIG. 2 is a perspective view, seen from another viewing angle, of one embodiment of a head coil, an adapter, and a patient support.
Figure 3:
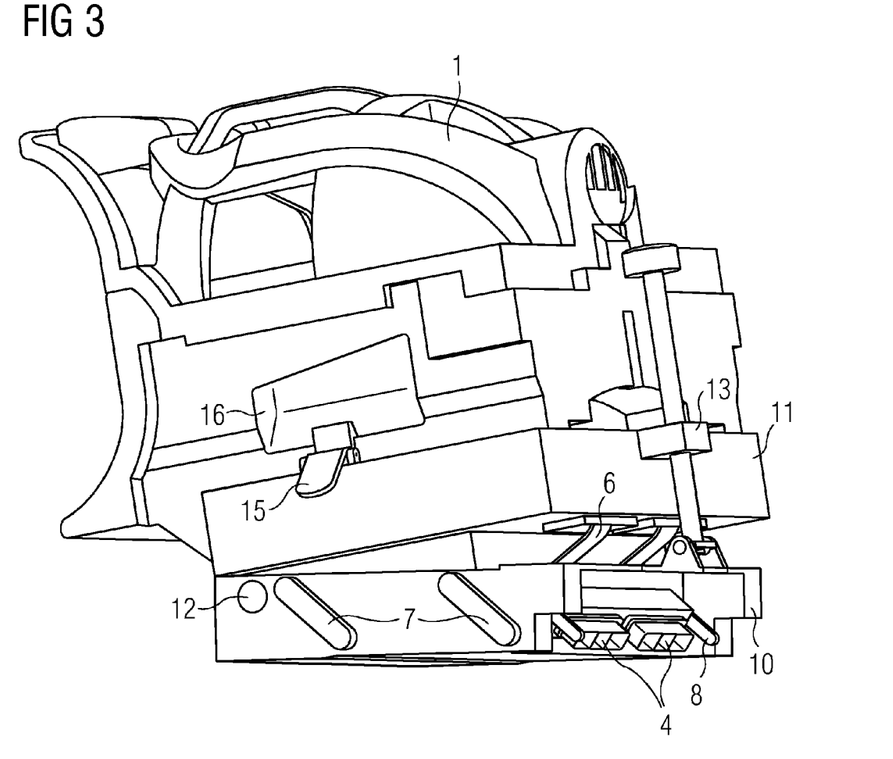
FIG. 3 is a perspective view from one side of one embodiment of a head coil and a removable adapter connected to the head coil.
Figure 4:
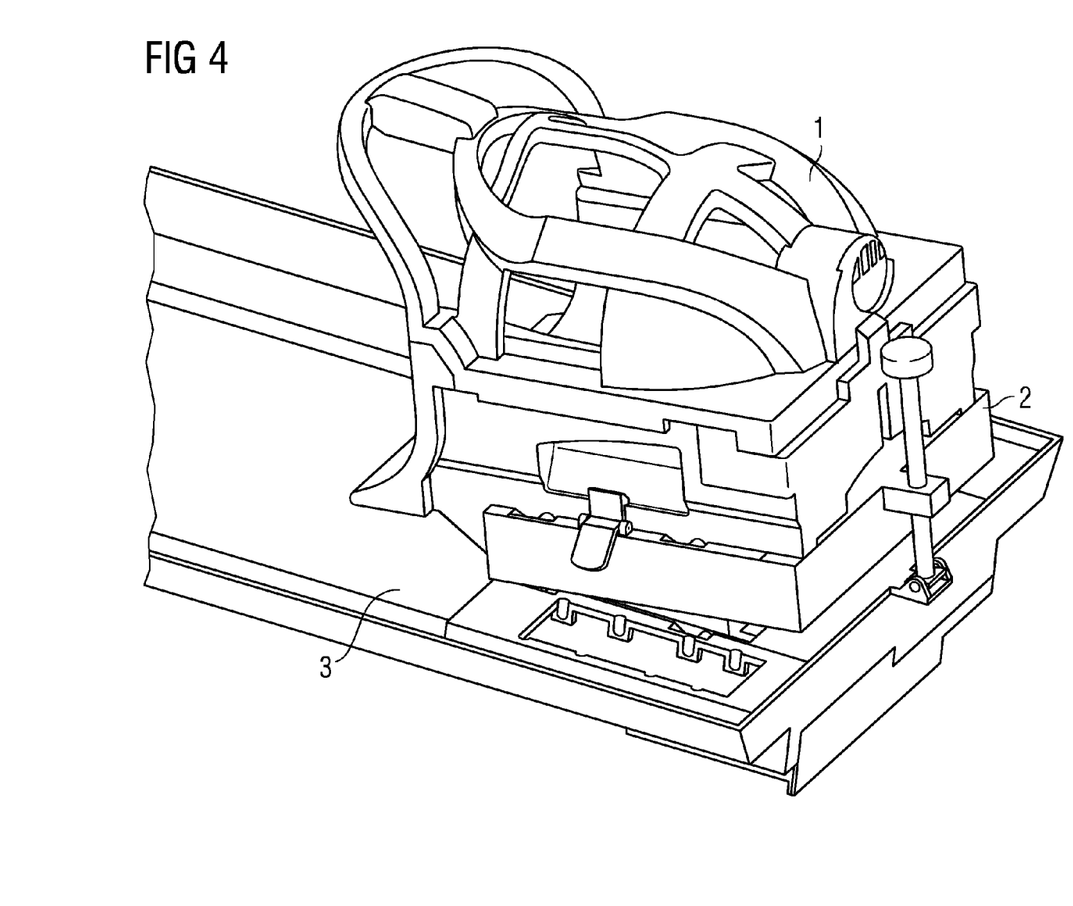
FIG. 4 is a perspective view of one embodiment of a head coil and a removable adapter connected to the head coil.
Figure 5:
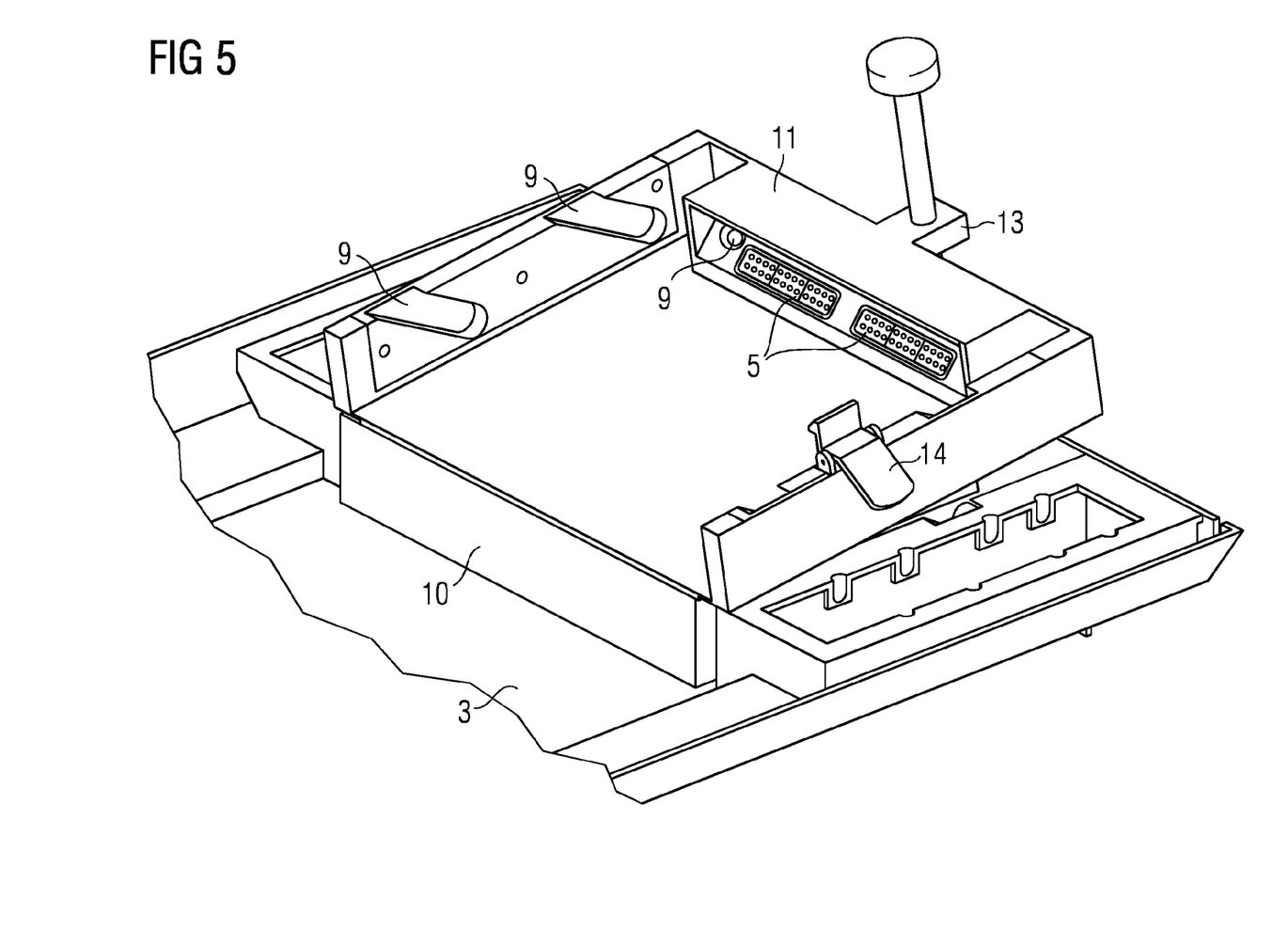
FIG. 5 is a perspective view of one embodiment of an adapter that is placed on a patient support and is removably connected to the patient support.

FIGS. 1 and 2 show, in perspective views from different directions, a head coil (on the left), an adapter (on the right; e.g., with a head coil-side adapter upper part 10 and a patient support-side adapter lower part 11), and a section of an MRT patient support 3 (at the bottom). FIG. 3 shows, in a perspective view from one side, a head coil of this type and an adapter 2 removably connected thereto. FIG. 4 shows, in a perspective view, a head coil of this type and an adapter 2 removably connected thereto, placed on a patient support 3 and removably (releasably) connected thereto. FIG. 5 shows a perspective view of an adapter 2 that is placed on a patient support 3 and is removably connected thereto.

Embodiments of an adapter 2 that is pluggable and thus may be placed in direct contact with power supply and/or data connections K-L (e.g., contacts) of a patient support, as shown, for example, in FIG. 1, and is pluggable and thus may be placed in direct contact with connections K-S (e.g., contacts) of a head coil 1 are described below. The embodiments enable, by virtue of the design thereof, positioning (movement) of a head coil with a head K of a patient relative to a patient support 2 for an MRT 101.

In the embodiments shown, the head K of a patient 105 may be moved from a relatively low position in relation to the patient support 3 into a relatively high position in relation to the patient support and may be or become fixed 13 at the relatively high position.

A directly contacted head coil 1, with the aid of an adapter 2 that is releasably (e.g., by unplugging and by releasing locking connections/screws) placed between the patient support 3 and the head coil, may be tilted and/or moved (y) in relation to the patient support 3.

The adapter 2 may be configured with a fixed tilt angle or with an adjustable tilt angle (e.g., using a plurality of locking positions on a spindle 13). The adapter 2 has electrical contacts 4 on the underside thereof. The electrical contacts 4 create an electrical connection to the patient support 3. Provided on an upper side of the patient support 3 are electrical contacts (e.g., plugs and/or sockets 5) that realize an electrical connection to the head coil.

The two contact sites (e.g., 4 and 5 toward the patient support and toward the head coil) on the adapter 2 are electrically connected in the interior of the adapter 2. The electrical connection 6 is configured, in the case of an adjustable adapter 2, by a flexible and/or sufficiently long conductor in order to maintain and compensate for the range of the angular adjustment. In a fixed embodiment of the adapter 2, this connection may be rigid.

The positioning or placement of the adapter 2 on the patient support 3 is carried out as with a conventional head coil 1, directly contacting the patient support (e.g., without the adapter). For this reason, the adapter 2 has, for example, the same guide elements (e.g., side guides 7 and guide lugs 8) on the side releasably (e.g., removably) connectable to the patient support 3 as a conventional head coil 1. The guide lugs 8 reduce the guidance play of the lateral guidance 7 and provide sufficient guidance accuracy for the lagging contact pins in contacts 4, 5.

Shown in the upper region of the adapter 2 is the contacting and guidance of the patient support for a head coil, in order to provide the same receptacle 9 for the head coil 1 that the head coil would conventionally have in the patient support. Direct plugging (e.g., of the contacts and possibly locking elements of a head coil on locking into a patient support) is reproduced 1:1 in the adapter.

The angular positioning between the adapter upper part 10 and the adapter lower part 11, and thus between the guides and the contacts, defines the inclined position (e.g., tilt) of the head coil relative to the patient support and/or the horizontal (e.g., plane x-z).

An embodiment of the adapter that is adjustable with regard to the angle thereof has a divided adapter housing including a support-side adapter housing lower part 10 and a coil-side adapter housing upper part 11. The two parts (e.g., parts 10, 11) of the adapter 2 may be adjusted relative to one another in the angle thereof via a rotary joint 12 and a drive 13.

A self-locking screw mechanism may be used as the drive.

The operation of the adapter 2 may be performed, for example, such that the adapter 2 is placed onto the head coil 1 remote from the patient support 3, is fastened to the head coil 1 with, for example, a snap connection 14 or another locking apparatus or by screws, and both parts (e.g., parts 1, 2) are placed together on the patient support 3 and contacted 4 therewith. The snap connection 14 has, for example, a movable snap hook 15 that engages behind an existing edge 16 in a head coil housing.

Alternatively, the adapter 2 may be plugged into the patient support 3, and the head coil may be plugged into the adapter 2. Using the described snap fastening 15, the head coil 1 and the adapter 2 are connected to one another and may be removed together from the patient support 3 following the examination. The adapter 2 is easily separable from the head coil 1 so that the head coil 1 may be used for patients, as required.

The embodiment of the adapter enables addition of the tilt function for ankylosing spondylitis patients into an existing system that has a directly contactable head coil. An existing patient support and an existing head coil may thus be used without modification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An adapter for a local coil for a magnetic resonance tomography device, the adapter being placeable on a patient support for the magnetic resonance tomography device, the adapter comprising:
    an adapter upper part that is removably connectable to the local coil;
    an adapter lower part that is removably connectable to the patient support; and
    a tilt device, by which the adapter upper part is movable relative to the adapter lower part.

2. The adapter as claimed in claim 1, wherein the adapter lower part has at least one connector for contacting, plugging, or contacting and plugging into a connector on the patient support.

3. The adapter as claimed in claim 2, wherein the at least one connector comprises a connector for a power supply to the local coil, for data, or a combination thereof.

4. The adapter as claimed in claim 1, wherein the adapter upper part comprises at least one connector for contacting, plugging into, or contacting and plugging into a connector on the local coil.

5. The adapter as claimed in claim 4, wherein the at least one connector comprises a connector for a power supply to the local coil, for data, or a combination thereof.

6. The adapter as claimed in claim 1, wherein the local coil is a head coil, and wherein the adapter is an adapter for the head coil.

7. The adapter as claimed in claim 1, wherein the local coil comprises a head coil, the head coil comprising at least one housing support surface configured to provide for the head of a patient being laid onto the at least one housing support surface, an upper part of the head coil forming a chamber, into which the head of the patient fits, with the at least one housing support surface, or a combination thereof.

8. The adapter as claimed in claim 1, further comprising a screw mechanism operable for manual or motor-driven height adjustment of the adapter upper part relative to the adapter lower part.

9. The adapter as claimed in claim 1, further comprising a spindle that has a rotary joint fastened to the adapter lower part, the spindle extending through a nut that is firmly connected to the adapter upper part, the adapter upper part being movable relative to the adapter lower part by rotation of the spindle.

10. The adapter as claimed claim 1, wherein the adapter lower part has guides, the guides being configured in order to guide the adapter lower part on guide receptacles of the patient support.

11. The adapter as claimed claim 10, wherein the guides comprise bolts or axles.

12. The adapter as claimed claim 1, wherein the adapter upper part comprises receptacles for guides of the local coil, the guides being configured to guide the local coil relative to the adapter upper part.

13. The adapter as claimed in claim 1, wherein in order to move the adapter lower part relative to the adapter upper part, a pinion wheel, a toothed rack, a cable pulley mechanism, a lead screw mechanism, or a combination thereof is provided.

14. The adapter as claimed in claim 1, further comprising a self-locking positioning device provided on the adapter lower part and the adapter upper part.

15. The adapter as claimed in claim 1, further comprising flexible conductor connections provided between contacts on the adapter lower part and on the adapter upper part.

16. The adapter as claimed in claim 1, wherein in a state plugged together with the patient support, the adapter provides through contacting of electrical contacts of the adapter to electrical contacts of the patient support.

17. The adapter as claimed in claim 1, wherein the local coil comprises a head coil, and
wherein in a state plugged together with the head coil, the adapter provides through contacting of electrical contacts of the adapter to electrical contacts of the head coil.

18. The adapter as claimed in claim 1, wherein the local coil comprises a head coil, and
wherein the adapter further comprises:
on an underside of the adapter, a replica of a direct plugging arrangement and a replica of guide elements of the head coil; and
on an upper side of the adapter, a replica of a direct plugging arrangement and a replica of guide elements of the patient support.

19. The adapter as claimed in claim 1, wherein the local coil comprises a head coil, and
wherein the adapter is operable to fix a tilt angle of the head coil once set relative to the patient support or to the horizontal.

20. The adapter as claimed in claim 1, wherein the local coil comprises a head coil, and
wherein the adapter further comprises a lockable connection, a snap connection, or the lockable connection and the snap connection provided on the adapter for connecting to the head coil.

21. The adapter as claimed in claim 1, wherein the adapter upper part is an adapter-head coil connecting part, and
wherein the adapter lower part is an adapter-patient support connecting part.

22. The adapter as claimed in claim 1, wherein the local coil comprises a head coil, and wherein the head coil is placeable on the adapter.

23. The adapter as claimed in claim 22, wherein the head coil is placeable on the adapter such that at least one surface, edge, point, or a combination thereof of the head coil lie on the adapter, and
wherein the adapter is placeable on the patient support such that at least one surface, edge, point, or a combination thereof of the adapter lie on the patient support.

24. A head coil for a magnetic resonance tomography device, the head coil comprising:
an adapter for the head coil, the adapter being placeable on a patient support for the magnetic resonance tomography device, the adapter comprising:
an adapter upper part that is removably connectable to the local coil;
an adapter lower part that is removably connectable to the patient support; and
a tilt device, by which the adapter upper part is movable relative to the adapter lower part.

* * * * *